US005616752A

United States Patent [19]

Patsidis et al.

[11] Patent Number: 5,616,752
[45] Date of Patent: Apr. 1, 1997

[54] METALLOCENES AND PROCESSES THEREFOR AND THEREWITH

[75] Inventors: Konstantinos Patsidis; Bernd Peifer; Helmut G. Alt, all of Bayreuth, Germany; Rolf L. Geerts, Bartlesville, Okla.; Darryl R. Fahey, Bartlesville, Okla.; M. Bruce Welch, Bartlesville, Okla.; Syriac J. Palackal, Bartlesville, Okla.; Harold R. Deck, Bartlesville, Okla.

[73] Assignee: Phillips Petroleum Company, Bartlesville, Okla.

[21] Appl. No.: 462,328

[22] Filed: Jun. 5, 1995

Related U.S. Application Data

[62] Division of Ser. No. 402,244, Mar. 10, 1995, Pat. No. 5,565,592, which is a division of Ser. No. 154,224, Nov. 17, 1993, Pat. No. 5,466,766, which is a continuation-in-part of Ser. No. 75,712, Jun. 11, 1993, Pat. No. 5,399,636, Ser. No. 75,931, Jun. 11, 1993, Pat. No. 5,347,026, Ser. No. 984,054, Nov. 30, 1992, Pat. No. 5,393,911, Ser. No. 734,853, Jul. 23, 1991, Pat. No. 5,436,305, and Ser. No. 697,363, May 9, 1991, Pat. No. 5,191,132.

[51] Int. Cl.$^6$ ............................ C07F 17/00; C07F 7/00
[52] U.S. Cl. ........................ 556/95; 556/465; 556/478; 556/489; 556/160; 556/943; 502/152; 502/158; 585/359
[58] Field of Search .................. 556/95, 465, 478, 556/489; 585/359; 502/152, 158; 526/160, 943

[56] References Cited

U.S. PATENT DOCUMENTS 4,530,914  7/1985  Ewen et al. ............................ 502/113
4,808,561  2/1989  Welborn, Jr. .......................... 502/104
4,892,851  1/1990  Ewen et al. ........................... 502/104
5,145,819  9/1992  Winter et al. ......................... 502/117
5,329,033  7/1994  Spaleck et al. ........................ 556/53
5,391,789  2/1995  Rohrmann ............................. 556/11

OTHER PUBLICATIONS

Mirek et al., J. Organomet Chem., vol. 248, pp. 107–122 (1983).

Primary Examiner—Porfirio Nazario-Gonzalez
Attorney, Agent, or Firm—Edward L. Bowman

[57] ABSTRACT

A method is provided for forming a supported cyclopentadiene-type compound comprising contacting a cyclopentadiene-type compound containing an active halogen with an inorganic support having surface hydroxyl group. Also there is provided a method of preparing a supported metallocene comprising reacting the supported cyclopentadiene-type compound with a transition metal compound under suitable conditions. There is also provided a process for producing bridged cyclopentadiene-type ligands having a bridge having branch that has a terminal vinyl group. Also metallocenes of these ligands are provided. Still further there is provided a process for producing bridged cyclopentadiene-type ligands having a bridge having a branch that has a terminal active halogen. The resulting new ligands and supported metallocenes produced therefrom are also provided. There is further provided supported metallocene catalysts wherein at least two metallocenes of differing effectiveness are both bonded to an inorganic support having surface hydroxy groups. Olefin polymerization employing the inventive bridged supported metallocenes is also provided, as well the resulting polymer products.

8 Claims, No Drawings

METALLOCENES AND PROCESSES THEREFOR AND THEREWITH

This application is a division of application Ser. No. 08/402,244 filed Mar. 10, 1995 now U.S. Pat. No. 5,565,592 which is a division of application Ser. No. 08/154,224 filed Nov. 17, 1993 now U.S. Pat. No. 5,466,766 which is a continuation-in-part of U.S. patent application Ser. No. 08/075,712 filed Jun. 11, 1993 now U.S. Pat. No. 5,399,636; U.S. patent application Ser. No. 08/075,931 filed Jun. 11, 1993 now U.S. Pat. No. 5,347,026; now U.S. patent application Ser. No. 07/984,054 filed Nov. 30, 1992 now U.S. Pat. No. 5,393,911; now U.S. patent application Ser. No. 07/734,853 filed Jul. 23, 1991 now U.S. Pat. No. 5,436,305 and a CIP of Ser. No. 07/697,363 filed May 9, 1991, now U.S. Pat. No. 5,191,132. The disclosures of all the above-mentioned applications are incorporated herein by reference.

FIELD OF THE INVENTION

The present invention relates to a metallocene composition, a process for preparing the composition, and a process for using the composition. The present invention also relates to organic compounds suitable for making metallocenes.

BACKGROUND OF THE INVENTION

Since the discovery of ferrocene in 1951, a number of metallocenes have been prepared by the combination of anions having the cyclopentadienyl structure with various transition metals. The term "cyclopentadienyl structure" as used herein refers to the following structure.

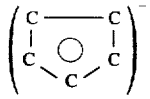

Such "cyclopentadienyl structure" can be formed by addition of various metal alkyls to cyclopentadiene and "cyclopentadiene-type" compounds.

The term "cyclopentadiene-type compound" as used herein refers to compounds containing the cyclopentadiene structure. Examples of cyclopentadiene-type compounds include unsubstituted cyclopentadiene, unsubstituted indene, unsubstituted tetrahydroindene, unsubstituted fluorene, and substituted varieties of such compounds.

Many of the cyclopentadiene-type metallocenes have been found useful in catalyst systems for the polymerization of olefins. It has been noted in the art that variations in the chemical structure of such cyclopentadienyl-type metallocenes can have significant effects upon the suitability of the metallocene as a polymerization catalyst. For example, the size and substitutions on cyclopentadienyl-type ligands have been found to affect the activity of the catalyst, the stereoselectivity of the catalyst, the stability of the catalyst, and other properties of the resulting polymer; however, the effects of various substituents is still largely an empirical matter, that is, experiments must be conducted in order to determine just what effect a particular variation will have upon a particular type of cyclopentadienyl-type metallocene. Some examples of some cyclopentadienyl-type metallocenes are disclosed in U.S. Pat. Nos. 4,530,914; 4,808,561; and 4,892,851, the disclosures of which are incorporated herein by reference.

In the past most polymerization work has been done using homogeneous, i.e. soluble, metallocenes rather than heterogeneous systems in which the metallocene is insoluble during the polymerization. However, for many industrial applications it would be desirable to have insoluble supported forms of metallocenes that are still active as polymerization catalysts.

It is also envisioned that such heterogeneous catalysts would have other uses. For example, the compositions could possibly be used as catalysts for hydrogenation, alkene epoxidation, alkene isomerization, ketone reduction, stereoselective alkene polymerization, and as reagent for stereoselective cobalt-mediated reactions, alkyltitanium addition reactions with aldehydes, and formation of allylic amines.

Accordingly, an object of the present invention is to provide methods for producing such heterogeneous catalysts. Still another object is to provide novel organic compounds suitable for use in preparing metallocenes.

An object of the present invention is thus to provide certain new organic compounds, including bridged ligands and metallocenes. Another object of the present invention is to provide a method for preparing new organic compounds including bridged ligands and metallocenes. A further object of the present invention is to provide supported, bridged ligands and metallocenes. Yet a further object of the present invention is to provide a process for preparing the supported, bridged ligands and metallocenes. Still another object of the present invention is to provide polymerization catalysts employing the supported metallocenes. Yet another object of the present invention s to provide processes for the polymerization of olefins using the supported metallocene catalyst systems. Still yet another object of the present invention is to provide polymers produced using such supported, metallocene catalysts.

SUMMARY OF THE INVENTION

In accordance with the present invention there is provided a method for forming a supported cyclopentadiene-type compound comprising contacting a cyclopentadiene-type compound containing an active halogen with an inorganic support having surface hydroxyl group. Also in accordance with the present invention there is provided a method of preparing a supported metallocene comprising reacting the supported cyclopentadiene-type compound with a transition metal compound under suitable conditions to form said supported metallocene.

Still further in accordance with the present invention there is provided a process for producing bridged cyclopentadiene-type ligands having a bridge having at least one branch having olefinic unsaturation. Metallocenes of such ligands are also provided. In accordance with yet another embodiment of the present invention there is provided a process for producing bridged cyclopentadiene-type ligands having a bridge having at least one branch that has an active halogen. The resulting new ligands and supported metallocenes produced therefrom are also provided.

In accordance with another aspect of the present invention there is provided supported metallocenes wherein at least two metallocenes of differing activity are both bonded to an inorganic support having surface hydroxy groups.

According to another embodiment of the invention, a process for olefin polymerization is provided which comprises contacting an olefin under olefin polymerization conditions with a composition comprising the inventive bridged supported metallocene prepared as described above, optionally, in combination with a suitable activator. According to yet another embodiment of the invention there is provided a polymer product resulting from such a polymerization process.

DETAILED DESCRIPTION OF THE INVENTION

A wide variety of cyclopentadiene-type compounds having active halogens are suitable for the present invention. Included are bridged cyclopentadiene compounds in which two cyclopentadiene-type compounds are bound together by a bridge having an active halogen as well as unbridged cyclopentadiene compounds in which a cyclopentadiene-type compound has a radical having an active halogen. Examples of the latter include such compounds of the formula $$Z\text{—}A\text{—}X_n$$

wherein Z is a cyclopentadiene type radical; A is Si, Ge, Sn; and X is selected from hydrogen, hydrocarbyl radicals, and halogens; wherein at least one X is a halogen, and n is a number filling the remaining valence of A. The hydrocarbyl radicals are other than cyclopentadiene type radicals and generally contain 1 to 8 carbon atoms. Some specific examples of such compounds include cyclopentadienyl dimethyl silyl chloride, fluorenyl dimethyl silyl chloride, indenyl dimethyl silyl chloride, fluorenyl ethyl chloride, fluorenyl dimethyl methyl chloride, fluorenyl methylene chloride, fluorenyl diphenyl germane chloride, fluorenyl diphenyl tin chloride, fluorenyl silyl trichloride, fluorenyl germane trichloride, fluorenyl methyl germane dichloride and the like, including such compounds in which the cyclopentadiene-type group contains one or more substituents. The currently preferred active halogen compound are silyl halides.

The unbridged cyclopentadiene-type compounds can be prepared using the general procedures disclosed in the aforementioned U.S. patent applications Ser. No. 75,931; Ser. No. 734,853; and Ser. No. 697,363, the disclosures of which are incorporated herein by reference.

Examples of bridged ligands include compounds of the formula Z—R'—Z wherein each Z can be the same or different substituted or unsubstituted cyclopentadiene-type radical and R' is a structural bridge linking the two Z's, wherein R' contains at least one active halogen. Some such bridged ligands can be made using the general techniques taught in U.S. Pat. No. 5,191,132 and pending U.S. application Ser. No. 734,853. For example, an alkali metal salt of a cyclopentadiene-type compound can be reacted with a bridge precursor compound X—R'—X wherein each X is a halide and wherein R' contains at least one active halide, to produce either a bis (cyclopentadienyl-type) bridged compound or a mono (cyclopentadienyl-type) compound of the formula Z—R'—X which is then reacted with an alkali metal salt of a different Z compound to produce a bridged compound of the formula Z—R+—Z wherein the two Z's are different. Examples of X—R'—X include trihalogenated compounds of Si, Ge, and Sn.

Some specific examples of silyl bridged ligands having active halogen include for example 1-cyclopentadienyl-9-fluorenyl methylchlorosilane, bis (9-fluorenyl)phenylchlorosilane, and bis(2,8-difluoro-9-fluorenyl)methylchlorosilane.

In a particularly preferred embodiment the bridge R' of the ligand Z—R+—Z has a branch extending outwardly from the divalent R' radical, which branch contains a halosilyl group. Typically, the branch would be an alkyl branch containing 2 to 12 carbon atoms, more commonly, 2 to 5 carbon atoms. Some examples of such halogenated branched bridged compounds include 2-(bis-9-fluorenyl-methylsilyl)-1-trichlorosilylethane; 1-chlorodimethyl silyl-5-cyclopentadienyl-5-(9-fluorenyl)hexane; and 5-cyclopentadienyl-5-(9-fluorenyl)-1-trichlorosilylhexane.

Halogenated branched bridged ligands can be prepared by the halogenation, i.e. chlorination, or hydrosilylation of a suitable bridged ligand which has a branch having olefinic unsaturation. Examples of such bridged compounds include those in which the R' bridge has a branch of the formula R"$_2$C=CH—(R''')$_n$—wherein R''' is a hydrocarbyl radical having 1 to 10 carbon atoms, n is 1 or 0, and each R" is the same or different and selected from the group consisting of hydrocarbyl radicals having 1 to 10 carbon atoms and hydrogen. One of the embodiments of the present invention provides such olefinic branched bridged cyclopentadienyl compounds.

Such olefinic branched ligands can be prepared by reacting a dihalo olefinic silane with an alkali metal salt of a suitable cyclopentadiene-type compound to produce an compound of the formula Z—R+—Z wherein each Z is the same or alternatively to first produce a compound of the formula Z—R'—X wherein X is a halogen and then reacting that compound with an alkali metal salt of another different cyclopentadiene-type compound to produce a compound of the formula Z—R+—Z wherein the two Z's differ. Such reactions can be carried out using conditions of the type disclosed in U.S. Pat. 5,191,132. The resulting olefinic branched ligands can then be reacted with chlorosilanes or chloroalkyl silanes to produce branched bridged ligands in which the branch has an active terminal halogen. The hydrosilyation reaction can be carried out using conditions such as disclosed by J. L. Speier in *Adv. Organomet Chem.*, 49, 1849 (1984).

An alternate technique for forming a olefinic branched bridged ligand involves reacting a carbonyl compound having olefinic unsaturation with cyclopentadiene in the presence of pyrrolidine and methanol to yield an alkenyl fulvene which is then reacted with an alkali metal salt of a cyclopentadiene compound, such as, for example, fluorenyl to yield the unsaturated-branched-bridged ligand containing two cyclopentadienyl-type groups, i.e. fluorenyl and cyclopentadienyl. For example, one could react 5-hexene-2-one with cyclopentadiene using a procedure like that disclosed by Stone et al in *J. Org. Chem.*, 49, 1849 (1984) to yield 6-(3-butenyl)-6-methylfulvene which could then be reacted with fluorenyllithium and subsequently by hydrolyzed to yield 5-cyclopentadienyl-5-(9-fluorenyl)-1-hexene. The terminal alkenyl group can then be subjected to hydrosilyation as described in the preceding paragraph.

The present invention thus envisions vinyl terminated branched bridged ligands of the formula

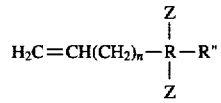

wherein n is a number typically in the range of about 0 to 10: R is Si, Ge, C, or Sn; R" is selected from hydrogen, or alkyl groups typically having 1 to 10 carbon atoms, or aryl groups typically having 6 to 10 carbon atoms. The present invention thus also envisions the halogenation and hydrosilyation reaction products of such vinyl terminated compounds as well as the metallocenes of such vinyl terminated compounds.

The metallocenes of such olefinic unsaturated branched-bridged ligands can be prepared by reacting the branched-bridged bis(cyclopentadienyl-type) ligand with an alkali metal alkyl to produce the divalent ligand salt that is then reacted with the transition metal compound to yield the metallocene, using the techniques generally known in the art for forming such metallocenes. See for example, European Published Application 524,624 which corresponds to pending U.S. application Ser. No. 734,853.

The inorganic support materials having surface hydroxyl groups include inorganic oxides, carbonates such as chalk, silicates such as talc, clay, and the like. Some particularly preferred supports include silica, alumina, clay, phosphated alumina, and mixtures thereof.

Phosphated aluminas can be prepared by the steps comprising: (1) mixing aluminum nitrate with a phosphate compound, in the presence of water, to form a solution; (2) adding a basic compound, preferably in aqueous form, to the solution to produce a solid product; (3) recovering the solid product; (4) optionally, washing the solid product with a solvent to prepare a washed-product; (5) drying the solid product or washed product, resulting in a dried product; and (6) calcining the dried product to produce the phosphated alumina. Suitable phosphate compounds include, but are not limited to ammonium phosphate (dibasic), ammonium phosphate (monobasic), sodium phosphate (monobasic), sodium phosphate (dibasic), magnesium phosphate, potassium phosphate (dibasic), potassium phosphate (monobasic), manganese phosphate, and mixtures thereof. The presently preferred phosphate compound is ammonium phosphate (monobasic) because of its ready availability and easy of use. Suitable basic compound employed in step (2) should be able to produce a precipitate from the solution. Examples of suitable basic compound include, but are not limited to, ammonium hydroxide, lithium hydroxide, sodium hydroxide, sodium carbonate, sodium bicarbonate, potassium hydroxide, magnesium hydroxide, barrium phenoxide, calcium hydroxide, calcium phenoxide, RONa, RSNa, and mixtures thereof wherein R is a $C_1-C_6$ alkyl radial. The presently preferred basic compound is ammonium hydroxide. The solvent used in step (4) to wash the solid product can be an alcohol, ether, ketone, acid, amide, or water, as long as it does not react with or solubilize the solid product. Examples of suitable solvents include, but are not limited to, water, methanol, ethanol, propanol, isopropanol, butanol, isobutanol, pentanol, diethyl ether, tetrahydrofuran, acetone, methyl ethyl ketone, acetic acid, dimethylforamide, and mixtures thereof. The presently preferred solvents are water and ethanol because of their ready availability. The drying of step (5) can be a conventional drying or drying under reduced pressure. The drying temperature can vary widely from about 50° C. to about 150° C. under about 0.05 mmHg to about 800 mmHg pressure for about 1 to about 30 hours, preferably from 60° C. to 100° C. under 0.05 to 760 mmHg pressure for 5 to 20 hours. The calcining step can also vary widely from about 250° C. to about 30 minutes to about 1500° C., preferably 500° C. to 1000° C., under atmospheric pressure for about 15 hours, preferably 1 to 7 hours.

In the preparation of the phosphated alumina, the molar ratio of the phosphate compound to aluminum nitrate is generally in the range of from about 0.05:1 to about 5:1, preferably from about 0.1:1 to about 2:1, and most preferably from 0.2:1 to 1:1 for best physical form and catalytic activity of phosphated alumina when used as a component of the invention composition. The molar ratio of water to aluminum nitrate is in the range of from about 10:1 to about 200:1, depending on the solubility of both aluminum and the phosphate compound, preferably about 20:1 to about 100:1, most preferably 25:1 to 50:1. The molar ratio of the basic compound to aluminum nitrate is in the range of from about 0.05:1 to about 10:1, preferably about 0.2:1 to about 5:1 and most preferably 0.5:1 to 2:1. The recovery of the solid product in step (3) can be carried out by any known means such as, for example, filtration, decantation and centrifugation. The molar ratio of the washing solvent to aluminum nitrate can vary widely from about 5:1 to about 1000:1 depending on the type of solvent used. The washing can also be carried out more than once and/or with a different solvent.

Examples of clays include, but are not limited to, kaolinite, halloysite, vermiculite, chlorite, attapulgite, smectite, montmorillonite, illite, saconite, sepiolite, palygorskite, Fuller's earth, and mixtures thereof. The presently preferred clay is a montmorillonite clay. The presently most preferred clay is sodium montmorillonite which is generally known as bentonite.

Examples of porous oxides or mixed oxides of silicon and/or aluminum include those having a specific surface area of 50 to 1,000 sq.m./g, more generally 100 to 800, and more preferably 150 to 650 sq.m./g, and whose pore volume is in the range of 0.2 to 3, preferably 0.4 to 3, in particular 0.6 to 2.7 cm3/g. Such supports would generally have an average particle size in the range of about 1 to about 500 millimicron, more typically about 10 to about 200, and more preferably about 20 to 100 millimicron. Depending upon the specific surface area and the temperature pretreatment, the hydroxyl group number of such supports is in the range of about 0.5 to about 50 mmol, more typically about 1 to about 20, and more preferably about 1.5 to about 10, hydroxyl groups per gram of support.

The bridged or unbridged cyclopentadiene-type compound having an active halogen is reacted with the hydroxyl-containing support under suitable reaction conditions to obtain a supported cyclopentadiene-type compound.

Generally before reacting the support with the halogenated cyclopentadiene-type compound, it is preferable to remove adsorptively bound water from the support by drying at a temperature in the range of from about 120 to about 800 degrees C., more typically about 200 to about 500 degrees C. The drying can be monitored analytically by titrating the OH content of the support material against n-butylmagnesium chloride. After drying, the support can be stored under an inert gas, for example, nitrogen or argon to exclude air and water.

The present invention thus provides a process which comprises contacting a bridged ligand having the formula of Z—R+—Z with an inorganic material Q to form a bridged ligand which is chemically bonded to the inorganic moiety Q, wherein each Z can be the same or different, substituted or unsubstituted, hydrocarbyl radical having an active hydrogen selected from the group consisting of cyclopentadienyl, indenyl, tetrahydroindenyl, fluorenyl, and mixtures thereof; R' is a bridge having a reactive halogen atom, and Q is an inorganic moiety having surface hydroxyl groups such as, for example, silica, alumina, clay, phosphated alumina, and mixtures thereof.

It is also within the scope of the present invention to contact two or more bridged ligands of that type with the inorganic support. It is also within the scope of the present invention to form supported ligands containing two or more unbridged cyclopentadienyl-type ligands or a mixture of the unbridged and bridged ligands. In an especially preferred embodiment two or more active halogen-containing ligands are used which have differing effects upon polymerization.

The conditions employed for contacting of the bridged or unbridged active halogen-containing ligand and the inorganic material can vary over a wide range. Typically, such is done in the presence of a liquid diluent, preferably a solvent for the ligand. Most preferably, the reaction is carried out in the presence of a basic compound which will neutralize any acid formed during the reaction. A typical example would be pyridine. The molar ratio of the ligand to the inorganic material can also vary over a wide range. Generally the molar ratio of the ligand to the OH on the surface of the inorganic material would be in the range from about 1:1 to about 0.00001:1.

The resulting supported cyclopentadienyl-type compound can then be used to form a supported metallocene. Preferably the supported cyclopentadienyl-type compound is subjected to purification to remove any undesirable by-products that might have been produced during its preparation. Techniques such as extraction, solvent washing, and evaporation can be used.

To form the supported metallocene the supported cyclopentadienyl-type compound is then reacted with an organo alkali metal compound to form the corresponding supported cyclopentadienyl alkali metal salt which is then reacted with a suitable transition metal compound under suitable conditions. Typically transition metal halide compounds are employed of the formula MeXn wherein Me is a transition metal selected from metals of Groups IIIB, IVB, VB, and VIB of the Periodic Table and n is a number reflecting the valence of the metal, generally 3 or 4. Each X in the formula can be the same or different and can be selected from the group consisting of halogens, and hydrocarbyl or hydrocarbyloxy groups having 1 to about 20 carbon atoms. Preferably at least one of the X's is a halogen. The preferred transition metal compounds are those of the metals selected from the group consisting of Ti, Zr, Hf, Sc, Y, V, and La. The presently most preferred metals are Ti, Zr, V, or Hf. Some examples of such transition metal compounds include zirconium tetrachloride, hafnium tetrachloride, cyclopentadienyl titanium trichloride, cyclopentadienyl zirconium trichloride, cyclopentadienyl methyl zirconium dichloride, fluorenyl zirconium dichloride, 3-methylcyclopentadienyl zirconium trichloride, 4-methylfluorenyl zirconium trichloride, indenyl methyl zirconium dichloride, and the like.

When the supported ligand is a non-bridged ligand it is generally necessary to react it with a cyclopentadienyl-type-containing transition metal compound to form the metallocene, for example cyclopentadienyl zirconium trichloride, cyclopentadienyl dimethyl zirconium chloride, fluorenyl dimethyl zirconium chloride, or cyclopentadienyl methyl zirconium dichloride. In any case, the reaction can be carried out using the same general techniques that have been used in the past to form the unsupported form of such metallocene. Generally, this involves forming an alkali metal salt of the supported cyclopentadienyl-type compound and reacting it with a transition metal halide compound in the presence of a suitable solvent.

If the unbridged ligand contains residual active halogen groups, it is generally desirable to react the supported ligand with enough organoalkali metal compound so that the active halide will be replaced with the organic radical of the organoalkali metal compound before the reaction is begun to prepare the metallocene. The presently preferred organoalkali metal compounds, used here as in forming cyclopentadienyl salts to form metallocenes, are aliphatic or aromatic salts of lithium or sodium.

Some illustrative, but non-limiting examples of bridged supported metallocenes within the scope of the present invention include, for example, silica-O-1-cyclopentadienyl-1-cyclopentadienylmethylsilane zirconium dichloride, silica-O-bis (9-fluorenyl)phenylsilane zirconium dichloride, silica-O-1-cyclopentadienyl-9-fluorenylmethylsilane hafnium dichloride, silica-O-bis(9-fluorenyl)phenylsilane hafnium dichloride, silica-O-1-cyclopentadienyl-9-fluorenylmethylsilane vanadium dichloride, silica-O-bis(9-fluorenyl)phenylsilane vanadium dichloride, silica-O-1-cyclopentadienyl-9-fluorenylmethylsilane titanium dichloride, silica-O-bis(9-fluorenyl)phenylsilane titanium dichloride, silica-O-bis(2,8-difluoro-9-fluorenyl)methylsilane zirconium dichloride, silica-O-1-cyclopentadienyl-9-fluorenylmethylsilane zirconium dichloride, alumina-O-cyclopentadienyl-9-fluorenylmethylsilane zirconium dichloride, bentonite-O-1-cyclopentadienyl-9-fluorenylmethylsilane zirconium dichloride, and mixtures thereof. The presently preferred bridged metallocene is silica-O-1-cyclopentadienyl-9-fluorenylmethylsilane zirconium dichloride. In the names given in this paragraph the phrase silica-O-merely refers to the fact that the bridged metallocene is bonded through the bridge to a surface oxygen of the support.

Some examples of supported unbridged metallocenes include silica-O-dimethyl silyl cyclopentadienyl-fluorenyl zirconium dichloride, silica-O-diphenyl silyl cyclopentadienyl-cyclopentadienyl zirconium dimethyl, and the like.

Some specific examples of the bridged ligands that can be used in the present invention include those having the formula of

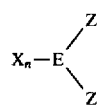

wherein each Z can be the same or different, substituted or unsubstituted, hydrocarbyl radical selected from the group consisting of cyclopentadienyl, indenyl, tetrahydroindenyl, fluorenyl, and mixtures thereof; E is a bridge connecting the two Z's and is selected from the group consisting of C, Si, Sn, Ge, B, Al, N, or P; each X can be the same or different and is selected from the group consisting of hydrogen, fluorine, chlorine, bromine, iodine, R, OR, $NR_2$, $PR_2$, or mixtures thereof, wherein R is a $C_1$ to $C_{20}$ hydrocarbyl radical, wherein at least one X is a halide, and wherein n is a number sufficient to fill the valences of E, generally 1 or 2.

Under one embodiment of the present invention, a substituted or unsubstituted cyclopentadienyl-type hydrocarbon, Z, having an acidic, replaceable hydrogen atom is contacted with an organolithium and an organohalosilane. Z is the same as that disclosed above. The presently preferred hydrocarbons having an acidic, replaceable hydrogen are cyclopentadiene, indene, tetrahydroindene, fluorene, or mixtures thereof. The preferred organolithium is an alkyllithium including butyllithium, methyllithium, ethyllithium, propyllithium, or mixtures thereof. The presently most preferred organolithium is butyllithium. The presently preferred organohalosilane is an alkylhalosilane or arylhalosilane such as methyltrichlorosilane, ethyltrichlorosilane, propyltrichlorosilane, phenyltrichlorosilane, tolyltrichlorosilane, or mixtures thereof. The presently most preferred organohalosilanes are methyltrichlorosilane, phenyltrichlorosilane, or mixtures thereof.

This first step of this embodiment of the invention can be carried out in the presence of a suitable solvent. Examples of suitable solvents include, but are not limited to diethyl ether, tetrahydrofuran, hydrocarbons such as pentane, hexane, heptane, cyclohexane, and toluene, and the like. According to the present invention, the reaction pressure and temperature for this embodiment are not particularly critical and can vary over a wide range. Atmospheric pressure is presently preferred although higher or lower pressures can be employed. Typically, the reaction temperature is in the range of from about −100° C. to about 100° C. Generally, it is convenient to carry out the first step at ambient temperatures.

The molar ratio of the hydrocarbon having at least two acidic, replaceable hydrogens to the organolithium can vary over a wide range depending on the results desired and is generally in the range of from about 5:1 to about 1:5, preferably about 2:1 to about 1:2, and most preferably about 1:1. Similar molar ratios can be employed for the organohalosilane to the lithiated hydrocarbon. The molar ratio of the solvent to the organolithium is generally in the range of from about 1000:1 to about 0.1:1, preferably about 500:1 to about 0.5:1.

The ligand formed during the first step having the formula of $Z-EX_{n+1}$ wherein the scopes of E and X are the same as those disclosed above except that one X must be a halogen and n is an integer of 1 or 2, can be then contacted with an organo alkali metal compound having the formula of ZMa wherein Z is the same as described above and Ma is an alkali metal. The presently preferred organo alkali metal compounds represented by the formula of ZMa include cyclopentadienylsodium, indenylsodium, tetrahydroindenylsodium, fluronenylsodium, cyclopentadienyllithium, indenyllithium, tetrahydroindenyllithium, flurorenyllithium, or mixtures thereof. The reaction conditions can be the same as those disclosed for the preparation of the halogenated compound of the formula $Z-EX_{n+1}$. This step can also be carried out in the presence of a solvent. The scope of the solvent is the same as described above. The molar ratio of the ligand to the organo alkali metal compound can vary in a wide range and is generally in the range of from about 5:1 to about 1:5, preferably from about 2:1 to about 1:2, and most preferably about 1.2:1 to 1:1.2. The molar ratio of the solvent to the organo alkali metal compound can be generally the same as that described for the solvent to the organolithium in the first step of this embodiment of the invention.

A bridged ligand having the formula of Z—EX —Z, wherein Z, E, X, and n are the same as those described above except that one X is a halogen, is formed in the second step of this embodiment of the process. In the third step of this embodiment of the process, the bridged ligand thus formed is contacted with an inorganic material. The inorganic material is generally used as catalyst support and has the same scope as described above. This results in a bridged ligand chemically bonded to the inorganic support. The bridged ligand chemically bonded to an inorganic support can then be further contacted with an organolithium and a metal halide having the formula of $MX_m$, in the fourth step of this embodiment of the process, under conditions to form a bridged metallocene, wherein M is a metal selected from Ti, Zr, Hf, Sc, Y, V, or La; m is a number sufficient to fill out the remaining valences of the metal M; and each X can be the same or different, and is selected from the group consisting of alkyl groups, hydrogen, fluorine, chlorine, bromine, and iodine. The reaction conditions for this step can also generally be the same as those described for the first step. Similarly, a solvent can also be present in this step of the invention. The scope of the solvent can be the same as that in the first step and the molar ratio of the solvent to the organolithium in this step is the same as that of the solvent to the organolithium in the first step. The molar ratio of the bridged ligand to the organolithium can be in the range of from about 5:1 to about 1:5, preferably from about 3:1 to about 1:3, and most preferably about 1:2. The molar ratio of the organolithium to the metal halide is generally about 2:1.

The supported metallocenes resulting from this invention can be recovered and purified using conventional techniques known in the art such as filtration and extraction. It is generally desirable to recover the metallocene in a form that is free of any substantial amount of by-product impurities. Since the stability of the various metallocenes varies, it is generally desirable to use the metallocenes soon after their preparation or at least to store the metallocene under conditions favoring their stability. For example the metallocenes can generally be stored in the dark, at low temperature, i.e. below 0° C. and in the absence of oxygen or water.

The supported metallocenes can be used in combination with a suitable activator for the polymerization of olefinic monomers.

Examples of suitable activator include generally, organoaluminoxane, tris-perfluorophenyl borate, trityl tetra-perfluorophenyl borate, and any of those organometallic co-catalysts which have in the past been employed in conjunction with transition metal containing olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethyl aluminum, tri-isobutyl aluminum, diethyl aluminum chloride, diethyl aluminum hydride, and the like.

The currently most preferred activator is an organoaluminoxane. Such compounds include those compounds having repeating units of the formula

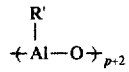

where R' is an alkyl group generally having 1 to 5 carbon atoms; and p is a number between 0 to about 100, preferably about 5 to about 50, and most preferably 10 to 40. The presently most preferred organoaluminoxane is methylaluminoxane. Organoaluminoxanes, also sometimes referred to as poly(hydrocarbyl aluminum oxides) are well known in the art and are generally prepared by reacting an hydrocarbylaluminum compound with water. Such a preparation techniques are disclosed in U.S. Pat. No. 4,808,561, the disclosure of which is incorporated herein by reference. The currently preferred co-catalysts are prepared either from trimethyl aluminum or triethylaluminum, sometimes referred to ns poly(methyl aluminum oxide) and poly(ethyl aluminum oxide), respectively. It is also within the scope of the invention to use an aluminoxane in combination with a trialkylaluminum, such as disclosed in U.S. Pat. No. 4,794, 096, the disclosure of which is incorporated herein by reference.

The supported metallocenes in combination with the organoaluminoxane activator can be used to polymerize olefins. Generally, it is within the scope of the present invention to carry out the polymerizations in the presence of supported forms of the catalyst and/or activator in a slurry or gas phase polymerization. It is within the scope of the invention to use a mixture of two or more metallocenes or a mixture of an inventive bridged metallocene with one or more other types of metallocenes.

The supported metallocenes when used with an organoaluminoxane are particularly useful for the polymerization of mono-unsaturated aliphatic alpha-olefins having 2 to 10 carbon atoms. Examples of such olefins include ethylene, propylene, butene-1, pentene-1, 3-methylbutene-1, hexene-1, 4-methylpentene-1, 3-ethylbutene-1, heptene-1, octene-1, decene-1, 4,4-dimethyl-1-pentene, 4,4-diethyl-1-hexene, 3-4-dimethyl-1-hexene, and the like and mixtures thereof. The catalysts are particularly useful for preparing copolymers of ethylene or propylene and generally a minor amount, i.e. no more than about 12 mole percent, more typically less than about 10 mole percent, of the higher molecular weight olefin.

The polymerizations can be carried out under a wide range of conditions depending upon the particular metallocene employed, and the results desired. Examples of typical conditions under which the metallocenes can be used in the polymerization of olefins include conditions such as disclosed in U.S. Pat. Nos. 3,242,099; 4,892,851; and 4,530,914; the disclosures of which are incorporated herein by reference. It is considered that generally any of the polymerization procedures used in the prior art with any transition metal based catalyst systems can be employed with the present support bonded metallocenes.

Generally the molar ratio of the aluminum in the organoaluminoxane to the transition metal in the metallocene would be in the range of about 0.1:1 to about 03:1 and more preferably about 5:1 to about $10^4$:1. As a general rule, the polymerizations would be carried out in the presence of liquid diluents which do not have an adverse affect upon the catalyst system. Examples of such liquid diluents include butane, isobutane, pentane, hexane, heptane, octane, cyclohexane, methylcyclohexane, toluene, xylene, and the like. The polymerization temperature can vary over a wide range, temperatures typically would be in the range of about –60° C. to about 280° C., more preferably in the range of about 20° C. to about 160° C. Typically the pressure would be in the range of from about 1 to about 500 atmospheres or greater.

The polymers produced with this invention have a wide range of uses that will be apparent to those skilled in the art from the physical properties of the respective polymer. Some of the catalysts are useful for preparing syndiotactic polymers. The term syndiotactic polymer as used herein is intended to include those polymers having segments of more than 10 monomeric repeating units in which the alkyl group of each successive monomeric unit is on the opposite side of the plane of the polymer. Generally, the polymer segments having such syndiotactic microstructure are formed of at least about 40 monomeric repeating units in which the position of the alkyl group relative to the plane of the polymer alternates from one monomeric unit to the next monomeric unit.

EXAMPLES

A further understanding of the present invention, its various aspects, objects and advantages will be provided by the following examples. In these examples, all runs were routinely carried out using the Schlenk technique with the exclusion of oxygen and moisture. See generally, D. F. Shriver, The Manipulation of Air-sensitive Compounds, McGraw-Hill, 1969. Purified and dried argon served as protective gas. The solvents used were dried by distillation over a Na/K alloy (pentane, hexane, toluene, methylene chloride, ether and tetrahydrofuran) or phosphorus pentoxide under argon. Tetrahydrofuran was additionally purified over lithium alanate and methylene chloride was additionally purified over calcium hydride. Fluorene was purified over silica gel prior to use. Analogous procedures were followed for fluoranthene and phenanthrene. The propylene used for polymerization trials was purified for 1 hour at 30° C. using methylaluminoxane. An autoclave (1 liter) was used for the polymerization runs.

Example I

This example illustrates the preparation of a silica-bonded, bridged ligand.

Fluorene (20 g; 120 mmol) was dissolved in 200 mL of ether and slowly mixed with 76 mL of butyllithium (1.6M in hexane). After the evolution of gas had been completed, the mixture was stirred for 1 hour at room temperature and then the solvent was removed. Then solid fluorenyllithium was added in portions to a solution of 36 g (40 mL, 241 mmol) of methyltrichlorosilane in 700 mL of pentane. After completion of the addition, the mixture was stirred for a further period of 1 hour at room temperature and the reaction mixture was then filtered over sodium sulfate. The solution was concentrated by evaporation to 30% of its volume and crystallized at –30° C. The product, 9-fluorenylmethyldichlorosilane, was generated in the form of a white crystalline powder (yield: 95%).

9-Fluorenylmethyldichlorosilane (5 g; 17.9 mmol) was then dissolved in 100 ml of ether and the resulting solution was mixed with 1.6 g (18 mmol) of cyclopentadienyl sodium. After 4 hours of stirring at room temperature, the reaction mixture was filtered over sodium sulfate and the solvent was removed. A bright yellow crude product (1-cyclopentadienyl-9-fluorenylmethylchlorosilane) was obtained which contained 10% bisfluorenylmethylchlorosilane.

The crude product (5 g) obtained above was dissolved in 100 ml of toluene and the resulting solution was mixed with 5 g of silica gel (Merck No. 7713) and 10 ml of pyridine. The mixture was held for 34 hours at 80° C and then cooled to room temperature. The supernatant solution was decanted, the resulting product (silica-O-1-cyclopentadienyl-9-fluorenylmethylsilane) was washed several times with ether and then dried.

Example II

This example illustrates the preparation of a bridged metallocene chemically bonded to an inorganic support material.

The silica-O-1-cyclopentadienyl-9-fluorenylmethylsilane prepared in Example I was suspended or slurried in 100 ml of ether and mixed with 2 mole equivalents (20 ml) of butyllithium (1.6M in hexane) per silane. The reaction mixture was shaken for 24 hours at room temperature followed by washing several times with ether (100 ml). After the mixture was again suspended in 100 ml of ether, 5 g (1 mol equivalent) of zirconium tetrachloride per silane was added and the mixture was shaken for another 24 hours.

The reaction mixture was washed with ether as above and the suspension was filtered over sodium sulfate. A metallocene chemically bonded to silica, i.e. , silica-O-1-cyclopentadienyl-9-fluorenylmethylsilane zirconium dichloride was obtained.

Example III

This example illustrates the use of the bridged metallocene prepared in Example II as catalyst for olefin polymerization.

Ethylene polymerization was conducted for one hour at 90° C. in a 3.8 liter stirred, stainless steel reactor in the presence of isobutane diluent, hydrogen as a molecular weight control agent and methylaluminoxane as the co-catalyst. First the metallocene catalyst was weighed in a dry box and slurried in n-hexane to which a solution of methylaluminoxane has been added. One milliliter of the toluene methylaluminoxane solution was used. It was purchased from Schering at a concentration of 1.1M. The charge order was metallocene/methylaluminoxane slurry and then 2 liters of isobutane. After heating these materials to 90° C., 45 psi of hydrogen as determined from pressure drop in a 300 cc cylinder was introduced, and then ethylene was introduced so that the total reactor pressure was maintained at 435 psig for the entire hour. Ethylene was supplied on demand from a pressured reservoir as required during each run. Polymerization was terminated by venting ethylene and diluent. The polymer was recovered, dried and weighed to determine yields. Catalyst productivity is calculated by dividing polymer weight in grams by the weight of metallocene used in grams, or by the weight of metallocene plus methylaluminoxane in grams and is conveniently expressed as g polymer per g desired catalyst component per hour (g/g-hr).

The polymerization results are shown in Table I below.

TABLE I

| Run No. | Catalyst g | Yield g | Productivity (g/g-h) based on | |
|---|---|---|---|---|
| | | | Metallocene | Metallocene and MAO[a] |
| 1[b] | 0.5 | 0.4 | 8 | 3.5 |
| 2[c] | 0.5 | 1.5 | 30 | 13.2 |

[a]MAO, methylaluminoxane.
[b]The catalyst used in this run was silica-0-1-cyclopentadienyl-9-fluorenylmethyl silane zirconium dichloride.
[c]The catalyst used in this run was silica-0-1-cyclopentadienyl-9-fluorenylmethyl silane zirconium dichloride. This catalyst differed from run 1 in that the silica in run 2 was undried.

The results demonstrate that the supported, bridged metallocenes are useful as olefin polymerization catalyst.

Example IV 25 grams of fluorene was dissolved in 150 mL of diethyl ether and slowly reacted with 94 mL of a 1.6 molar solution of butyllithium in hexane. The reaction vessel was cooled in ice. The dark red solution from the reaction was stirred overnight at room temperature. Then 9.8 mL of dichloromethylvinylsilane was added. The reactor vessel was still cooled in ice. The reaction mixture was stirred 4 hours at room temperature and then mixed with 50 mL of water. The organic phase was dried over a sodium sulfate and the solvent was evaporated in a vacuum. The residue was dissolved in pentane and crystallized at −18° C. A white crystalline solid was obtained which was determined to be bis-9-fluorenylmethylvinylsilane. 1.80 g of the bis-9-fluorenylmethylvinylsilane was dissolved in 30 mL of trichlorosilane at room temperature. Approximately 1 milligram of hexachloroplatinic acid was added and a reaction mixture stirred overnight at room temperature. The solvent was evaporated in a vacuum. A white solid precipitated and was characterized as 2-(bis-9-fluorenyl-methylsilyl)-1-trichlorosilylethane.

Then 0.6 g of the 2-(bis-9-fluorenylmethylsilyl)-1-trichlorosilylethane was suspended in 20 mL of toluene along with 2.91 g of silica gel (Merck No. 7734) the silica gel had been dehydrated at 400° C.

The suspension also included 1 mL of pyridine. The reaction mixture was heated for 48 hours under reflux, the supernatant was then decanted and the silica gel was washed two times with 50 mL of methanol and five times with 50 mL of diethyl ether. The amount of supported bridged fluorenyl compound recovered was 3.16 g.

The recovered supported ligand was then suspended in 50 mL of diethyl ether and mixed with 20 mL of a 1.6 molar solution of n-butyl lithium in hexane. The reaction mixture was stirred for 48 hours at room temperature. The supernatant was then decanted and the residue washed five times with 50 mL of diethyl ether. Then the solid was combined with 50 mL of diethyl ether and 0.42 g of zirconium dichloride. That reaction mixture was stirred for 48 hours at room temperature and then a supernatant was decanted and the residue washed five times with 50 mL of diethyl ether. The resulting supported metallocene was then dried overnight in a drying cabinet. This will be referred to as supported catalyst 33.

Example V

In this synthesis 20.6 mL of cyclopentadiene and 11.7 mL of 5-hexene-2-one were dissolved in 100 mL of methanol. While cooling in ice 12.4 mL of pyrrolidine was added and the reaction mixture was stirred overnight at room temperature. Then 9.6 mL of glacial acidic acid was added. The reaction mixture was stirred for one half hour and then the solvent was evaporated in a vacuum. The residue was dissolved in 200 mL of diethyl ether and washed five times with 100 mL of water. The organic phase was filtered using a silica gel and dried over sodium sulfate. The solvent was evaporated in a vacuum. A yellow oil was recovered which was concluded to be 6-(3-butenyl)-6-methylfulvene.

A solution was prepared by dissolving 10 g of fluorene in 100 mL of THF and then this was slowly reacted with 37.6 mL of a 1.6 molar solution of n-butyllithium in hexane. This dark red solution was stirred overnight at room temperature. Then a solution was prepared by combining 8.8 g of 6-(butenyl)-6-methylfulvene with 50 mL of THF. This solution was then added dropwise over a period of one half hour to the solution of the fluorenyl lithium salt. That reaction mixture was stirred overnight at room temperature and then 100 mL of water was added. The organic phase was dried overnight over sodium sulfate and the solvent was evaporated in a vacuum. The yellow residue was dissolved in pentane and filtered using silica gel. The solvent was concentrated by means of evaporation. Crystallization took place at about −18° C. to give 5-cyclopentdienyl-5-(9-fluorenyl)-1-hexene in a form of a white solid.

Then 1.61 g of the bridged ligand having a vinyl terminated branch, i.e. 5-cyclopentadienyl-5-(9-fluorenyl)-1-hexene, was dissolved in 10 mL of chlorodimethylsilane at room temperature. Then approximately 1 mL of hexachloroplatinic acid was added and a reaction mixture stirred overnight at room temperature. The solvent was then evaporated in a vacuum. A white solid was recovered which was concluded to be 1-chlorodimethyl-silyl-5-cyclopentadienyl-5-(9-fluorenyl)-hexane. A portion of this material was then contacted with silica gel (Merck No. 7734) the process involved contacting 2 g of the silica gel dried as explained in Example IV and 1.56 g of the 1-chlorodimethyl-silyl-5-cyclopentadienyl-5-(9-fluorenyl)-hexane in a manner analogous to that used in the analogous step in Example IV. Then a supported zirconocene was prepared by reacting 1.74 g of that solid with 0.8 g of zirconium tetrachloride using a technique of the general type disclosed in Example IV. The resulting supported metallocene will be referred to herein as catalyst 34A.

Example VI

Another supported ligand was prepared by combining 4.11 g of silica gel (Merck No. 15111) and 2.96 g of 1-chlorodimethyl-silyl-5-cyclopentadienyl-5-(9-fluorenyl) hexane in a manner analogous to that described in Example V. About 4.4 g of this supported fluorenyl compound was recovered. Then 3.81 g of that supported fluorenyl compound was reacted with 1.75 g of zirconium tetrachloride in a manner analogous to that used performing the metallocene in Example IV. The recovered supported metallocene will be referred to herein as catalyst 34B.

Example VII

The supported zirconocene catalyst of Examples IV and V were evaluated for the polymerization of ethylene. The polymerizations were carried out in a 1 liter laboratory autoclave. The technique involved charging the autoclave with 500 mL of hexane and 10 mL of methylaluminoxane. The supported zirconocene was then suspended in toluene and mixed with methylaluminoxane and the added to the autoclave. The autoclave was thermostatically controlled at 60° C. and a constant ethylene pressure of 9 Bar was applied, the reaction was stopped after 1 hour. The results of these polymerizations are summarized in Table II below.

TABLE II

| Catalyst | Yield | g PE/g Metallocene-hr-bar |
| --- | --- | --- |
| 33 | 4 | 6 |
| 34a | 19 | 10 |
| 34b | 28 | 16 |

The results reveal that the supported metallocenes can be employed in the polymerization of ethylene.

Catalyst 34B was also evaluated for the polymerization of propylene. In this case 10 mL of methylaluminoxane was added to the autoclave and 500 mL of propylene was condensed into it. The contents were stirred for 30 minutes at 20 degrees C to dry the propylene. The supported zirconocene was again suspended in toluene along with methylaluminoxane and added to the autoclave. Again the reaction was carried out at 60° C. and interrupted after 1 hour. The reaction yielded 62 grams of polypropylene. The activity in terms of grams of polypropylene per grams of metallocene was 129.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the specification and the claims.

That which is claimed is:

1. A process for preparing a bridged cyclopentadienyl-type compound having a branch containing an olefinic group comprising reacting a dihalo olefinic silane with an alkali metal salt of a suitable cyclopentadiene-type compound to produce a compound of the formula Z—R+—Z wherein each Z is the same or alternatively to produce a compound of the formula Z—R'-X wherein X is a halogen and then reacting that compound with an alkali metal salt of another different cyclopentadiene-type compound to produce a compound of the formula Z—R'—Z wherein the two Z's differ, said Z's each being individually selected from the group consisting of cyclopentadienyl-type compounds and R' is the organic remnant of the dihalo olefinic silane.

2. A bridged cyclopentadienyl-type compound produced by the process of claim 1.

3. A bridged cyclopentadienyl-type compound of the formula

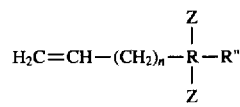

wherein said Z's are the same or different cyclopentadienyl-type radicals; n is a number in the range of about 0 to 10; R is Si, Ge, C, or Sn; R" is selected from hydrogen, or alkyl groups having 1 to 10 carbon atoms, or aryl groups having 6 to 10 carbon atoms.

4. The compound bis-9-fluorenylmethylvinylsilane.

5. A process for preparing a bridged cyclopentadienyl-type compound having a branch containing olefinic vinyl group comprising reacting a carbonyl compound having olefinic unsaturation with cyclopentadiene in the presence of pyrrolidine and methanol to yield an alkenyl fulvene which is then reacted with an alkali metal salt of a cyclopentadiene-type compound to yield the unsaturated-branched-bridged ligand containing two cyclopentadienyl-type groups.

6. A process according to claim 5 wherein 5-hexene-2-one is reacted with cyclopentadiene to yield 6-(3-butenyl)-6-methylfulvene which is then reacted with fluorenyllithium and then subjected to hydrolysis to yield 5-cyclopentadienyl-5-(9-fluorenyl )-1-hexene.

7. A bridged cyclopentadienyl-type compound produced by the process of claim 6.

8. The compound 5-cyclopentadienyl-5-(9-fluorenyl)-1-hexene.

\* \* \* \* \*

UNITED STATES PATENT AND TRADEMARK OFFICE
CERTIFICATE OF CORRECTION

PATENT NO.   : 5,616,752

DATED        : April 1, 1997

INVENTOR(S)  : Konstantinos Patsidis et al

It is certified that error appears in the above-identified patent and that said Letters Patent is hereby corrected as shown below:

Column 16, line 9, please delete "Z-R+-Z" and insert therefor ---Z-R'-Z---.

Signed and Sealed this

Fifth Day of August, 1997

Attest:

BRUCE LEHMAN

*Attesting Officer*        *Commissioner of Patents and Trademarks*